(12) United States Patent
Burrows et al.

(10) Patent No.: US 12,102,726 B2
(45) Date of Patent: Oct. 1, 2024

(54) DISINFECTING ASSEMBLY AND METHOD OF USING THE SAME

(71) Applicants: Martin John Burrows, South Haven, MI (US); Brian Scott Clemons, South Haven, MI (US)

(72) Inventors: Martin John Burrows, South Haven, MI (US); Brian Scott Clemons, South Haven, MI (US)

( * ) Notice: Subject to any disclaimer, the term of this patent is extended or adjusted under 35 U.S.C. 154(b) by 800 days.

(21) Appl. No.: 17/242,627

(22) Filed: Apr. 28, 2021

(65) Prior Publication Data

US 2022/0347332 A1 Nov. 3, 2022

(51) Int. Cl.
| | |
|---|---|
| *A61L 2/18* | (2006.01) |
| *A61L 2/22* | (2006.01) |
| *A61L 2/24* | (2006.01) |
| *B08B 3/04* | (2006.01) |
| *B08B 3/08* | (2006.01) |

(52) U.S. Cl.
CPC ............... *A61L 2/24* (2013.01); *A61L 2/18* (2013.01); *A61L 2/22* (2013.01); *B08B 3/08* (2013.01); *A61L 2202/14* (2013.01); *A61L 2202/15* (2013.01); *A61L 2202/16* (2013.01); *A61L 2202/17* (2013.01); *B08B 2203/02* (2013.01)

(58) Field of Classification Search
None
See application file for complete search history.

(56) References Cited

U.S. PATENT DOCUMENTS

| | | | |
|---|---|---|---|
| 3,444,867 | A | 5/1969 | Thornton |
| 3,698,029 | A | 10/1972 | Pulliam |
| 4,807,319 | A | 2/1989 | Poitevin |
| 5,133,375 | A | 7/1992 | Schinzing et al. |
| 5,285,802 | A | 2/1994 | Soderquist |
| 5,622,196 | A | 4/1997 | Luongo |
| 5,993,739 | A | 11/1999 | Lyon |
| 7,258,125 | B2 | 8/2007 | Holbrook |
| 7,346,956 | B2 | 3/2008 | Andre |
| 2003/0061674 | A1 | 4/2003 | Heinlein |

(Continued)

FOREIGN PATENT DOCUMENTS

KR 101043800 B1 * 6/2011

*Primary Examiner* — Jennifer A Leung (74) *Attorney, Agent, or Firm* — King & Partners, PLC (57) ABSTRACT

A disinfecting assembly that enables large mobile objects (e.g., grocery carts, shopping carts, carry out carts, wheelchairs, mobility scooters, etcetera) to be disinfected in a simple and effective manner, including: (1) a ground-engaging frame sub-assembly; (2) an energy source; (3) a reservoir, wherein the reservoir contains disinfecting fluid; (4) an output spray nozzle, wherein the output spray nozzle is associated with ground-engaging frame sub-assembly; (5) a fluid displacement pump; (6) a first conduit, wherein the first conduit is associated with the reservoir and the fluid displacement pump; (7) a second conduit, wherein the second conduit is associated with the fluid displacement pump and the output spray nozzle; (8) a motion sensor, wherein the motion sensor detects objects moving within the disinfecting assembly; and (9) a control box having a programmable logic controller, wherein the programmable logic controller is in electrical communication with the energy source, the fluid displacement pump; and the motion sensor.

1 Claim, 4 Drawing Sheets

(56) References Cited

U.S. PATENT DOCUMENTS

| | | | |
|---|---|---|---|
| 2005/0214159 A1* | 9/2005 | Schwei | A61L 2/24 422/28 |
| 2006/0107486 A1* | 5/2006 | Andre | B08B 3/022 15/345 |
| 2007/0272279 A1* | 11/2007 | Foster | A61L 2/18 134/32 |
| 2008/0210268 A1* | 9/2008 | Metheny | B60S 3/00 134/95.2 |

* cited by examiner

DISINFECTING ASSEMBLY AND METHOD OF USING THE SAME

CROSS-REFERENCE TO RELATED APPLICATIONS

This application claims the benefit of U.S. Provisional Application Ser. No. 63/067,822, entitled "AN APPARATUS FOR DISINFECTING LARGER ITEMS LIKE BUT NOT LIMITED TO SHOPPING CARTS," filed Aug. 19, 2020—which is hereby incorporated herein by reference in its entirety, including all references cited therein.

STATEMENT REGARDING FEDERALLY SPONSORED RESEARCH OR DEVELOPMENT

Not applicable.

REFERENCE TO A SEQUENCE LISTING

Not applicable.

BACKGROUND OF THE INVENTION

1. Field of the Invention

The present invention relates in general to disinfecting assemblies and, more particularly, to disinfecting assemblies that enable large mobile objects (e.g., grocery carts, shopping carts, carry out carts, wheelchairs, mobility scooters, etcetera) to be disinfected in a simple and effective manner. The present invention further relates to methods of using disinfecting assemblies to disinfect large mobile objects in a simple and effective manner.

2. Background Art

Washing, cleaning, sanitizing, and disinfecting assemblies and apparatuses have been known in the art for years and are the subject of a plurality of patents and publications, including: U.S. Pat. No. 7,346,956 entitled "Automatic Cart Wash Apparatus," U.S. Pat. No. 7,258,125 entitled "Shopping Cart Sanitizing System," U.S. Pat. No. 5,993,739 entitled "Continuous Washing System," U.S. Pat. No. 5,622,196 entitled "Apparatus for Washing Objects," U.S. Pat. No. 5,285,802 entitled "Portable Wheelchair Cleaning Apparatus," U.S. Pat. No. 5,133,375 entitled "Wheelchair Washer Apparatus," U.S. Pat. No. 4,807,319 entitled "Self-Contained High Pressure Hot Water Cleaning System for Grocery Carts," U.S. Pat. No. 3,698,029 entitled "Automatic Washing Apparatus," U.S. Pat. No. 3,444,867 entitled "Mobile Cart Washer," and United States Patent Application Publication Number 2003/0061674 entitled "Automatic Cart Washer"—all of which are hereby incorporated herein by reference in their entirety including all references cited therein.

U.S. Pat. No. 7,346,956 appears to disclose an automatic cart wash apparatus. The automatic cart wash apparatus provides improved cleaning of stock carts on a regular basis over manual cleaning by store employees. The automatic cart wash apparatus includes three main stages: a debris removal (vacuum) stage, a cleaning (wash, sanitize, rinse) stage, and a drying stage. The debris removal stage uses forced air and/or suction to remove solid and generally non-soluble waste, such as a paper or other trash and debris, from a stock cart. The cleaning stage uses a selection of detergents, sanitizing agents, and rinse agents to remove soluble or sticky waste, such as food and liquids, and to kill germs, viruses, and bacteria present on the cart. The drying stage removes excess liquids from the cart making it ready for use by the next customer.

U.S. Pat. No. 7,258,125 appears to disclose a system and method for removing contaminates from the surface of a shopping cart such as a grocery cart. The system includes subjecting the cart to multiple stages of disinfection, including washing, sanitizing, and drying stages. A shopping cart is subjected to these stages by conveying the cart on a conveyor system past a plurality of nozzles, which are configured to provide a disinfecting fluid such as water, sanitizer or air. The invention uses sensors to detect the location of a shopping cart during the sanitizing process. The sensors provide indications of the cart's location which may be used to control the operation of the disinfecting stages on the conveyor belt.

U.S. Pat. No. 5,993,739 appears to disclose a method for cleaning objects such as wheelchairs on a continuous basis. In one embodiment, the apparatus of the present invention is a mobile, self-contained system in which objects are cleaned and sanitized as they travel in a U-shaped path within a wash chamber. As the objects enter the first side of the wash chamber, suitably located water jets spray the objects with a mixture of detergent and water to remove associated foreign materials until shortly after the objects make a U-turn. At this point, the objects are first sprayed with a mixture containing a rinse agent and water, then with a spray containing disinfectant and water. The objects are thereafter dried by suitable drying means such as a high velocity air curtain system. The continuous washing system of the present invention preferably has a self-contained water heater to pre-heat the water prior to its being sprayed onto the objects. The system preferably also has a recycling path wherein water which has been sprayed onto the objects is collected and filtered in a water reservoir prior to being used again in the system.

U.S. Pat. No. 5,622,196 appears to disclose an apparatus for washing objects. The apparatus comprises a frame supporting a housing dimensioned to receive various, irregularly shaped objects. A conveyor belt having exterior sections that extend beyond the housing entrance and exit, conveys objects through the housing as a first series of nozzles spray the objects with a cleaning solution, Then, the objects are washed by a pair of high-speed rotating sprayer arms, mounted on the exterior sides of the housing, which direct pressurized water through circular cut out portions formed in the sides of the housing to the objects being conveyed through the housing. The objects are then rinsed by a second series of nozzles and subsequently exit the housing. The exterior sections of the conveyor belt are rotatable and are rotated toward the housing to form a compact configuration for transportation and storage.

U.S. Pat. No. 5,285,802 appears to disclose a wheelchair cleaning system that includes, in a modular assembly, a wash chamber, operators control unit and a mobile base support structure housing the electromechanical components used to apply the cleaning process. The operator places a wheelchair in the wash chamber and from the control unit selects cleaning functions to be applied through a programmable micro-processor. A pump draws cleaning solution from the sink through a line connected to the rotating spray arm assembly. As the spray arm lifts past the wheelchair, the solution is sprayed against the wheelchair through nozzles on the spray arm. The solution returns into the sink for continuous re-cycling. A drain pump draws the contaminated water from the sink through a drain line into a drain receptacle when the wash and rinse cycles are completed.

U.S. Pat. No. 5,133,375 appears to disclose a washer for a conventional wheelchair that has a washing chamber within an enclosure with fluid-driven rotatable washer arms having suitably angled nozzles for directing cleaning and rinsing fluids onto a wheelchair mounted on a slidable rack just above the slanted drain floor of the enclosure. The device also provides for rotating the large side support wheels during the washing cycles while keeping the chair from moving.

U.S. Pat. No. 4,807,319 appears to disclose a self-contained high pressure hot water cleaning system for grocery carts in which a trailer mounted fully enclosed system allows the automatic passage of individual grocery carts from one end to the other by the use of a conveyor passing through a wash tunnel having spray nozzles. The wash tunnel also provides a pair of rotating brushes, a spent fluid holding tank, a cleaning fluid supply tank, a sanitizing fluid supply tank, associated pumps as well as a heater for heating the cleaning fluid. The self-contained system further provides a hand operated wand at the entrance of the wash tunnel to allow an operator to remove difficult accumulation of grime from the grocery carts. A lifting table and exit ramp is also provided.

U.S. Pat. No. 3,698,029 appears to disclose an apparatus for automatically washing nestable shopping carts and the like. Automatic conveyor means separately engaging an undercarriage of each of a plurality of shopping carts for nested conveyance of the carts successively through a wash chamber and a rinse chamber of said apparatus. A plurality of rotatably mounted brushes, disposed about the conveyor means, are adapted to frictionally engage the moving carts in a scrubbing action. A counter-balanced, vertically movable and inclined array of wash nozzles forms a vertically-movable adaptable array, provided for accommodating and washing the undercarriage of shopping carts of different design and manufacture.

U.S. Pat. No. 3,444,867 appears to disclose a washer for grocery shopping type carts, having a wash station with nozzles mounted to spray a heated wash fluid at the cart, a continuous conveyor chain running through a track along the floor of the station with fingers for engaging the lower front part of the cart, a reservoir located below the station to receive wash fluid drained from the station, a recirculating pump for the wash fluid, and an elevating mechanism including a platform having one end pivotally attached near the floor of the wash station at the entry end and the distal end raised by a scissors-jack mechanism to lift a nested group of carts to the level of the floor of the wash station, where they feed by gravity toward the chain. When the foremost cart engages the chain, the engaged part of the cart is below the level of the beginning of the chain flight through the wash station, so that the cart is slightly lifted by the finger as it is pulled off the platform to disengage it from the remaining carts. The fingers are pivotally attached to the chain and constrained by the track to stand up from the chain to engage the cart. The track terminates at the exit of the wash station, removing the constraint on the fingers to assure positive release of the cart. A ramp having a bump in it to shake off water conducts the carts back to ground level.

United States Patent Application Publication Number 2003/0061674 appears to disclose an assembly for washing a golf cart that includes an enclosure having two openings and a floor. A conveyor system has a belt that attaches to the golf cart and extends along the floor. The conveyor system directs the golf cart through the enclosure. A connection to a water source is in fluid communication with a plurality of outlets positioned in an interior of the enclosure and positioned to direct water onto the golf cart as it passes through the enclosure. A drying means may be provided to remove excess water from the golf cart.

While the above-identified patents and publications do appear to disclose various washing, cleaning, sanitizing, and disinfecting assemblies and apparatuses, their configurations remain non-desirous and/or problematic inasmuch as, among other things, none of the above-identified assemblies and apparatuses appear to enable a user to disinfect large mobile objects (e.g., grocery carts, shopping carts, carry out carts, wheelchairs, mobility scooters, etcetera) in a simple and effective manner. To be sure, the above-identified patents and publications disclose complex, expensive, and maintenance intensive assemblies that are replete with drawbacks.

These and other objects of the present invention will become apparent in light of the present specification, claims, and drawings.

SUMMARY OF THE INVENTION

The present invention is directed to a disinfecting assembly that enables large mobile objects (e.g., grocery carts, shopping carts, carry out carts, wheelchairs, mobility scooters, etcetera) to be disinfected in a simple and effective manner, comprising: comprising, consisting essentially of, and/or consisting of: (1) a ground-engaging frame sub-assembly; (2) an energy source; (3) a reservoir, wherein the reservoir contains disinfecting fluid; (4) an output spray nozzle, wherein the output spray nozzle is associated with ground-engaging frame sub-assembly; (5) a fluid displacement pump; (6) a first conduit, wherein the first conduit is associated with the reservoir and the fluid displacement pump; (6) a second conduit, wherein the second conduit is associated with the fluid displacement pump and the output spray nozzle; (7) a motion sensor/photo eye, wherein the motion sensor detects objects moving within the disinfecting assembly; and (8) a control box having a programmable logic controller, wherein the programmable logic controller is in electrical communication with the energy source, the fluid displacement pump, and the motion sensor.

In a preferred embodiment of the present invention, the ground-engaging frame sub-assembly includes first and second horizontal support members each having a proximal section and a distal section, wherein the distal sections of the first and second horizontal support members are positioned in a spaced apart and parallel configuration and define an object pathway therebetween.

In another preferred embodiment of the present invention, the ground-engaging frame sub-assembly includes first and second horizontal support members each having a proximal section and a distal section, wherein the distal sections of the first and second horizontal support members are positioned in a spaced apart and parallel configuration and define an object pathway therebetween, and wherein the proximal sections are outwardly flared relative to the distal sections.

In yet another preferred embodiment of the present invention, the ground-engaging frame sub-assembly includes a first mounting member having a left vertical component, a right vertical component, a first L-bracket, a second L-bracket, and a top horizontal component positioned between the left and right vertical components, and a second mounting member having a left vertical component, a right vertical component, and a top horizontal component positioned between the left and right vertical components.

In one preferred embodiment of the present invention, the ground-engaging frame sub-assembly includes a first guard/ overspray panel secured to the first and second left vertical components, and a second guard/overspray panel secured to the first and second right vertical components.

In a preferred embodiment of the present invention, the energy source comprises alternating current and/or direct current (e.g., a primary and/or secondary electrochemical cell). When the energy source includes a primary and/or secondary electrochemical cell, it is preferably positioned within the control box.

In another preferred embodiment of the present invention, the disinfecting fluid comprises a solvent and a disinfecting agent. Additionally, the disinfecting fluid may also comprise a solvent, a disinfecting agent, a surfactant, and/or other adjunct agents.

In yet another preferred embodiment of the present invention, the fluid displacement pump, the control box, and the output spray nozzle are mounted to the first mounting member.

In one preferred embodiment of the present invention, the motion sensor is mounted to the first mounting member.

In a preferred embodiment of the present invention, the disinfecting assembly further comprises a pressure/flow regulator positioned between the reservoir and the output spray nozzle.

In another preferred embodiment of the present invention, the disinfecting assembly further comprises a positive pressure dryer mounted to the second mounting member.

BRIEF DESCRIPTION OF THE DRAWINGS

Certain embodiments of the present invention are illustrated by the accompanying figures. It will be understood that the figures are not necessarily to scale and that details not necessary for an understanding of the invention or that render other details difficult to perceive may be omitted.

It will be further understood that the invention is not necessarily limited to the particular embodiments illustrated herein.

The invention will now be described with reference to the drawings wherein.

DETAILED DESCRIPTION OF THE INVENTION

While this invention is susceptible of embodiment in many different forms, there is shown in the drawings and described herein in detail several specific embodiments with the understanding that the present disclosure is to be considered as an exemplification of the principles of the invention and is not intended to limit the invention to the embodiments illustrated.

It will be understood that like or analogous elements and/or components, referred to herein, may be identified throughout the drawings by like reference characters. In addition, it will be understood that the drawings are merely schematic representations of one or more embodiments of the invention, and some of the components may have been distorted from their actual scale for purposes of pictorial clarity.

Referring now to the collective drawings, and to FIGS. 1-4 in particular, disinfecting assembly 10, for disinfecting large mobile objects (e.g., grocery carts, shopping carts, carry out carts, wheelchairs, mobility scooters, etcetera) is shown as generally comprising ground-engaging frame sub-assembly 12, energy source 14; reservoir 16 for containing disinfecting fluid; output spray nozzle 18; fluid displacement pump 20; conduit 22; motion sensor/photo eye 24; and control box 26 having programmable logic controller 28.

Figure 1:
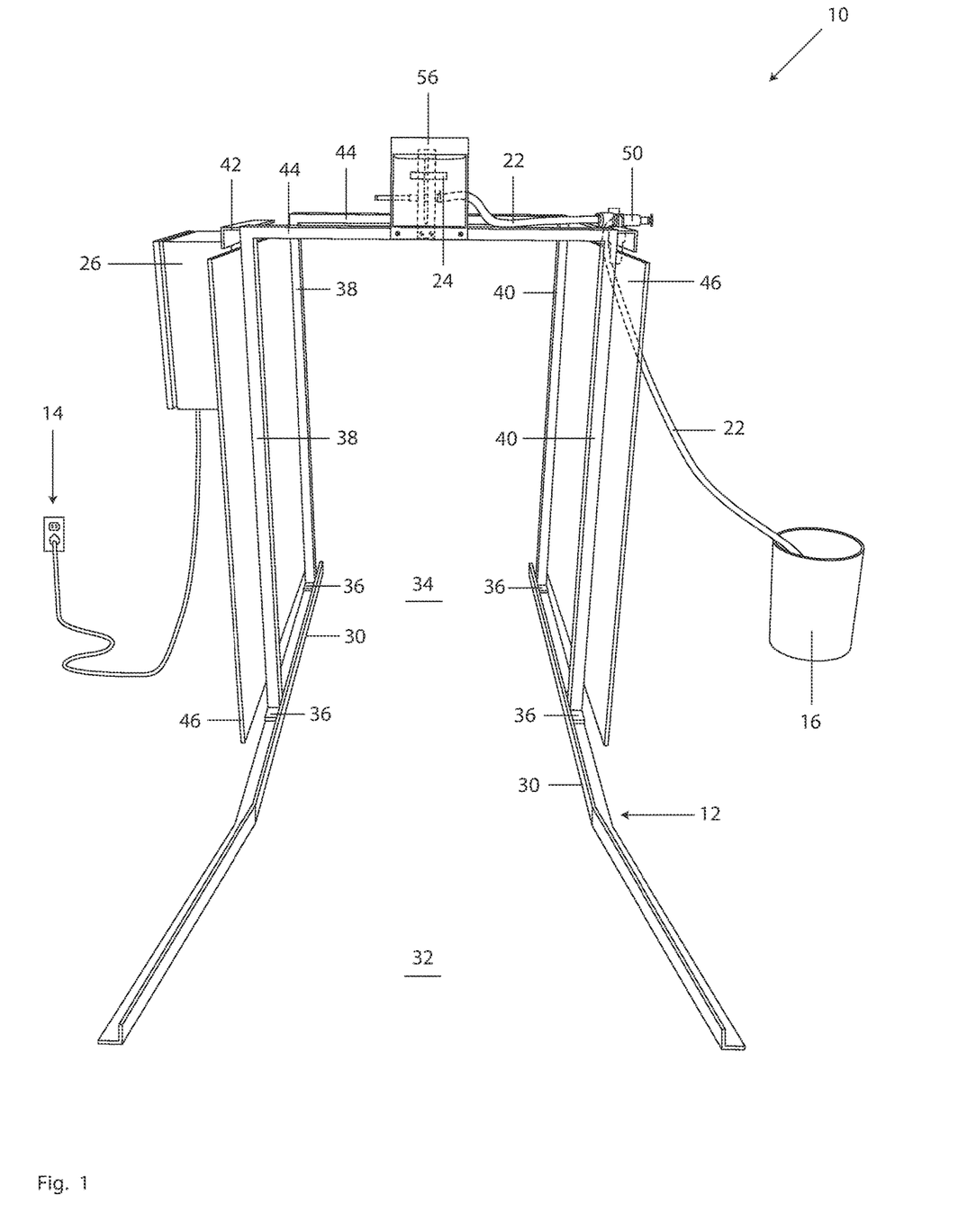
FIG. 1 of the drawings is a front perspective view of a disinfecting assembly in accordance with the present invention.
Figure 2:
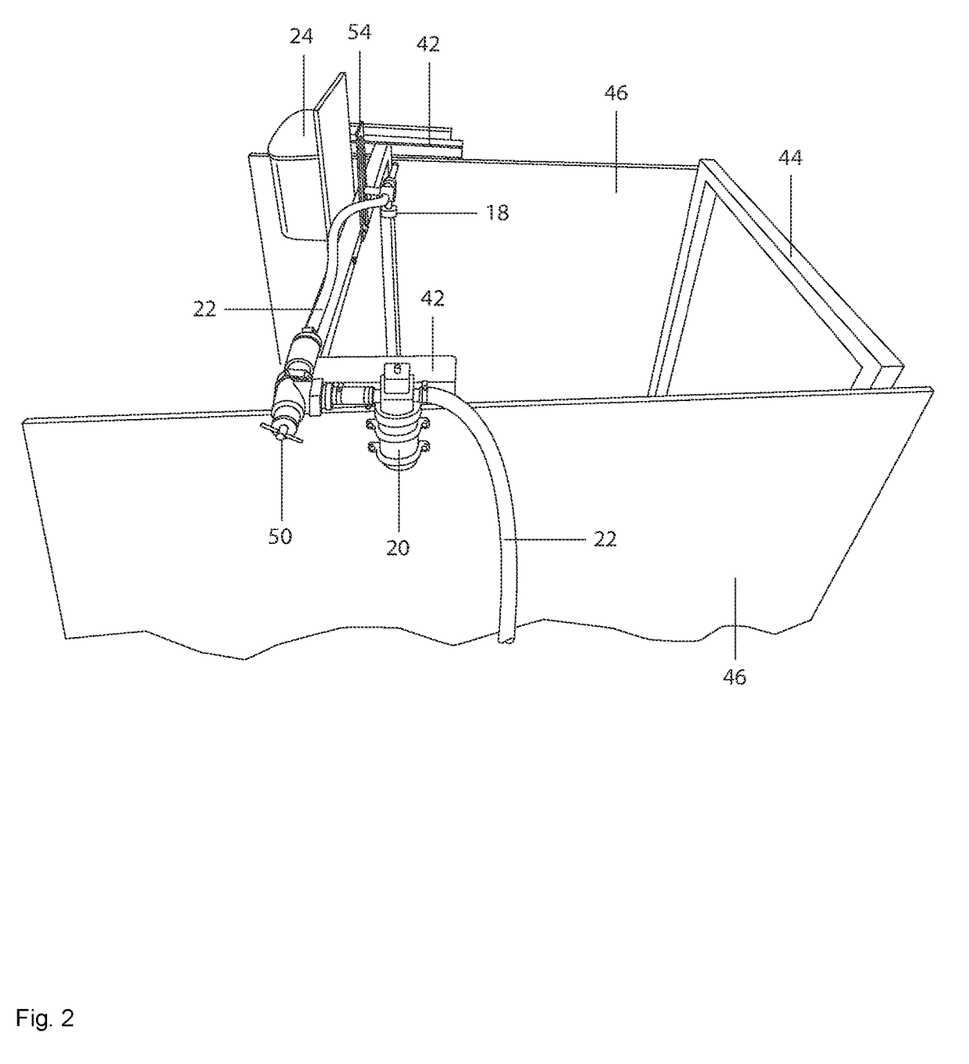
FIG. 2 of the drawings is an elevated, fragmented right-side view of the disinfecting assembly of FIG. 1.
Figure 3:
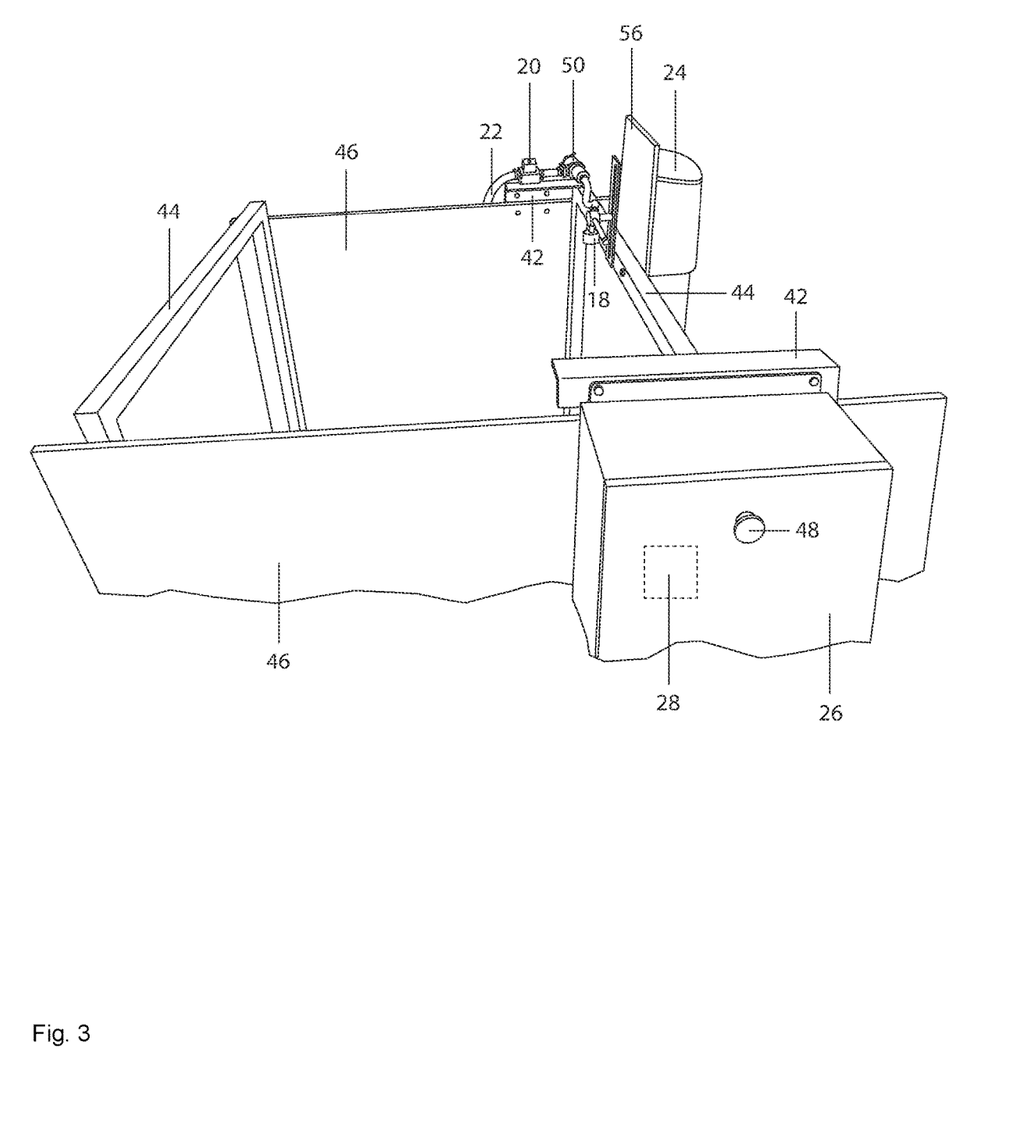
FIG. 3 of the drawings is an elevated, fragmented left-side view of the disinfecting assembly of FIG. 1.
Figure 4:
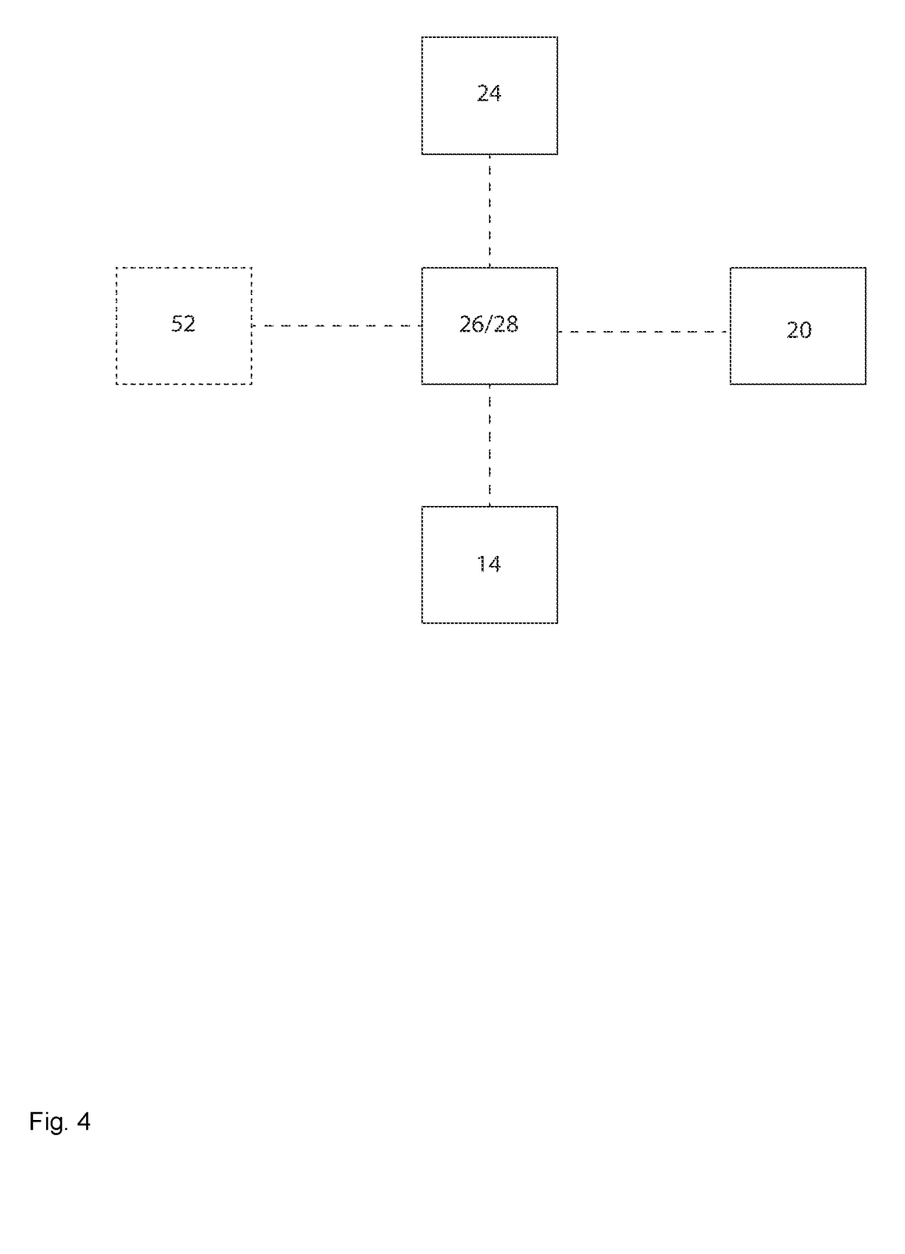
FIG. 4 of the drawings is a schematic representation of an electronics assembly for use in accordance with the present invention.

As is best shown in FIG. 1, ground-engaging frame sub-assembly 12 includes first and second horizontal support members 30, each having proximal sections and distal sections 32 and 34, respectively. The distal sections of the first and second horizontal support members are positioned in a spaced apart and parallel configuration and define an object or cart pathway therebetween. The proximal sections are outwardly flared relative to the distal sections to assist in collecting/funneling the objects to be disinfected.

Ground-engaging frame sub-assembly 12 includes first mounting member 36 having left vertical component 38, right vertical component 40, L-brackets 42, and top horizontal component 44, and second mounting member 36 having left vertical component 38, right vertical component 40, and top horizontal component 44.

In a preferred embodiment of the present invention, ground-engaging frame sub-assembly 12 includes first guard/overspray panel 46 secured to the first and second left vertical components, and second guard/overspray panel 46 secured to the first and second right vertical components.

In another preferred embodiment of the present invention, ground-engaging frame sub-assembly 12 is fabricated from a metal, a metal alloy, a natural resin, a synthetic resin, a plastic, a composite, wood, and/or combinations thereof.

Energy source 14 provides power to a plurality of the components of disinfecting assembly 10, including, but not limited to, fluid displacement pump 20, motion sensor 24, programmable logic controller (PLC) 28. Energy source 14 may include, for example, alternating current and/or direct current (e.g., a primary and/or secondary electrochemical cell). If energy source 14 includes a primary and/or secondary electrochemical cell, then it is preferably positioned inside of control box 26.

In accordance with the present invention, reservoir 16 preferably contains disinfecting fluid. In one embodiment, the disinfecting fluid comprises a solvent (e.g., a polar solvent (e.g., water, alcohols) and/or a non-polar solvent (e.g., heptane, hexane, benzene, etcetera) and a disinfecting agent (e.g., ethanol, isopropyl alcohol, a quaternary ammonium salt, etcetera). The disinfecting fluid may also comprise a surfactant (e.g., a cationic surfactant, an anionic surfactant, a nonionic surfactant, and/or a zwitterionic surfactant), a rheology modifier, a preservative, an adjunct agent—just to name a few.

Output spray nozzle 18 sprays the objects with the disinfecting fluid, and is preferably mounted to top horizontal component 44 of first mounting member 36. Output spray nozzle 18 is preferably secured to top horizontal component 44 via mounting bracket 54.

Fluid displacement pump 20 draws disinfecting fluid from reservoir 16 and displaces the same out of spray nozzle 18 and onto the object being disinfected. Preferably, fluid displacement pump 20 is mounted to first mounting member 36.

Conduit 22 is associated with reservoir 16, fluid displacement pump 20, and output spray nozzle 18. Conduit 22 may comprise hard line and/or flexible conduit.

Motion sensor/photo eye 24 observes when objects to be disinfected are translated through the disinfecting assembly 10 and, via communication with PLC 28, activates Fluid displacement pump 20 and a dryer if present. The PLC may be programmed for a plurality of run times (e.g., 1, 5, 10, 20, 30, 45, 60, 90, 120, 500+ seconds, etcetera). Motion sensor 24 is preferably mounted to the first mounting member. Motion sensor 24 is preferably secured to the first mounting member via mounting plate 56. It will be understood that motion sensor/photo eye 24 may be associated with and/or secured to any one of a number of components, including, but not limited to, any sub-component of ground-engaging frame sub-assembly 12, control box 26, and/or one or more guard/overspray panels 46—just to name a few.

Control box 26 preferably includes programmable logic controller 28. Programmable logic controller 28 is preferably in electrical communication with the energy source, the fluid displacement pump, the motion sensor, and the optional dryer (See FIG. 4). Control box 26 is preferably mounted to first mounting member 36. For safety purposes, control box 26 may also include emergency shut off 48.

In one embodiment of the present invention, disinfecting assembly 10 may further comprise pressure/flow regulator 50 preferably positioned between reservoir 16 and output spray nozzle 18.

Disinfecting assembly 10 may also optionally comprise positive pressure dryer 52. Positive pressure dryer 52 is preferably mounted to the second mounting member 36.

In operation, a user collects/provides one or more large mobile objects (e.g., grocery carts, shopping carts, carry out carts, wheelchairs, mobility scooters, etcetera) which may be stacked or nested. The user then simply pushes one or more carts through the disinfecting assembly where the motion sensor activates the components of the disinfecting assembly via the PLC. In particular, the cart(s) is first disinfected with the disinfecting fluid, and then optionally dried. After the cart(s) is disinfected and optionally dried, it is either stored or returned to service.

The foregoing description merely explains and illustrates the invention and the invention is not limited thereto except insofar as the appended claims are so limited, as those skilled in the art who have the disclosure before them will be able to make modifications without departing from the scope of the invention.

While certain embodiments have been illustrated and described, it should be understood that changes and modifications can be made therein in accordance with ordinary skill in the art without departing from the technology in its broader aspects as defined in the following claims.

The embodiments, illustratively described herein may suitably be practiced in the absence of any element or elements, limitation or limitations, not specifically disclosed herein. Thus, for example, the terms "comprising," "including," "containing," etcetera shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The phrase "consisting of" excludes any element not specified.

The present disclosure is not to be limited in terms of the particular embodiments described in this application. Many modifications and variations can be made without departing from its spirit and scope, as will be apparent to those skilled in the art. Functionally equivalent methods and compositions within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can of course vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etcetera. As a non-limiting example, each range discussed herein can be readily broken down into a lower third, middle third and upper third, etcetera. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member.

All publications, patent applications, issued patents, and other documents referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

Other embodiments are set forth in the following claims.

What is claimed and desired to be secured by Letters Patent of the United States is:

1. A disinfecting assembly, consisting of:
 a ground-engaging frame sub-assembly, wherein the ground-engaging frame sub-assembly includes first and second horizontal support members each having a proximal section and a distal section, wherein the distal sections of the first and second horizontal support members are positioned in a spaced apart and parallel configuration and define an object pathway therebetween, wherein the proximal sections are outwardly flared relative to the distal sections, wherein the ground-engaging frame sub-assembly includes a first mounting member having a left vertical component, a right vertical component, a first L-bracket, a second L-bracket, and a top horizontal component positioned between the left and right vertical components, and a second mounting member having a left vertical component, a right vertical component, and a top horizontal component positioned between the left and right vertical components, and wherein the ground-engaging frame sub-assembly includes a first guard/overspray panel secured to the left vertical components, and a second guard/overspray panel secured to the right vertical components;

an energy source, wherein the energy source includes 110 volts alternating current;

a reservoir, wherein the reservoir contains disinfecting fluid having a solvent and a disinfecting agent;

an output spray nozzle, wherein the output spray nozzle is mounted to the first mounting member;

a fluid displacement pump, wherein the fluid displacement pump is mounted to the first mounting member;

a pressure/flow regulator positioned between the reservoir and the output spray nozzle;

a first conduit, wherein the first conduit is associated with the reservoir and the fluid displacement pump;

a second conduit, wherein the second conduit is associated with the fluid displacement pump and the output spray nozzle;

a motion sensor, wherein the motion sensor detects objects moving within the disinfecting assembly, and wherein the motion sensor is mounted to the first mounting member;

a positive pressure dryer mounted to the second mounting member; and a control box having a programmable logic controller, wherein the control box is mounted to the first mounting member, and wherein the programmable logic controller is in electrical communication with the energy source, the fluid displacement pump, the motion sensor, and the positive pressure dryer.

* * * * *